(12) United States Patent
Wang et al.

(10) Patent No.: US 10,417,775 B2
(45) Date of Patent: Sep. 17, 2019

(54) METHOD FOR IMPLEMENTING HUMAN SKELETON TRACKING SYSTEM BASED ON DEPTH DATA

(71) Applicant: NANJING HUAJIE IMI TECHNOLOGY CO., LTD, Nanjing (CN)

(72) Inventors: Hang Wang, Nanjing (CN); Hao Liu, Nanjing (CN); Zan Sheng, Nanjing (CN); Gaofeng Yang, Nanjing (CN)

(73) Assignee: Nanjing Huajie IMI Technology Co., LTD., Nanjing (CN)

( * ) Notice: Subject to any disclaimer, the term of this patent is extended or adjusted under 35 U.S.C. 154(b) by 270 days.

(21) Appl. No.: 15/674,527

(22) Filed: Aug. 11, 2017

(65) Prior Publication Data
US 2018/0047175 A1  Feb. 15, 2018

(30) Foreign Application Priority Data
Aug. 12, 2016 (CN) .......................... 2016 1 0666231

(51) Int. Cl.
*G06K 9/00* (2006.01)
*G06T 7/246* (2017.01)
(Continued)

(52) U.S. Cl.
CPC ............ *G06T 7/251* (2017.01); *A61B 5/1128* (2013.01); *G06K 9/00* (2013.01); *G06K 9/00342* (2013.01);
(Continued)

(58) Field of Classification Search
CPC .... A61B 5/1128; G06K 9/00; G06K 9/00342; G06K 9/00369; G06T 2207/10024;
(Continued)

(56) References Cited

U.S. PATENT DOCUMENTS

2012/0056800 A1* 3/2012 Williams ................ G06F 3/011
345/156
2013/0278501 A1* 10/2013 Bulzacki ................. G06F 3/017
345/157

(Continued)

FOREIGN PATENT DOCUMENTS

| CN | 102831380 | 12/2012 |
| CN | 101789125 | 10/2013 |
| CN | 103399637 | 11/2013 |

*Primary Examiner* — Xin Jia
(74) *Attorney, Agent, or Firm* — JCIPRNET

(57) ABSTRACT

The present invention relates to a method for implementing a human skeleton tracking system based on depth data, specifically applied to a human skeleton tracking system based on depth data which is composed of a data acquisition unit, a limb segmentation unit, a skeleton point unit, and a tracking display unit. The units are in a relationship of sequential invocation. The limb segmentation unit uses scene depth data obtained after processing by the data acquisition unit to perform limb segmentation. The skeleton point unit uses the result obtained after segmentation by the limb segmentation unit to compute specific positions of respective skeleton points of a limb. The tracking display unit uses the positions of the skeleton points computed by the skeleton point unit to establish a skeleton model of the human body and perform tracking display.

5 Claims, 13 Drawing Sheets

(51) Int. Cl.
 *G06T 7/194* (2017.01)
 *G06T 7/11* (2017.01)
 *A61B 5/11* (2006.01)
 *G06T 3/40* (2006.01)

(52) U.S. Cl.
 CPC ............ G06K 9/00369 (2013.01); G06T 7/11 (2017.01); G06T 7/194 (2017.01); *G06T 3/40* (2013.01); *G06T 2207/10024* (2013.01); *G06T 2207/10028* (2013.01); *G06T 2207/30196* (2013.01); *G06T 2210/12* (2013.01)

(58) Field of Classification Search
 CPC . G06T 2207/10028; G06T 2207/30196; G06T 2210/12; G06T 3/40; G06T 7/11; G06T 7/194; G06T 7/251
 See application file for complete search history.

(56) References Cited

U.S. PATENT DOCUMENTS

| | | | | |
|---|---|---|---|---|
| 2014/0334670 | A1* | 11/2014 | Guigues | G06T 7/251 382/103 |
| 2015/0310629 | A1* | 10/2015 | Utsunomiya | A61B 5/11 382/107 |
| 2016/0151696 | A1* | 6/2016 | Chen | A63B 69/3614 473/199 |

* cited by examiner

METHOD FOR IMPLEMENTING HUMAN SKELETON TRACKING SYSTEM BASED ON DEPTH DATA

CROSS-REFERENCE TO RELATED APPLICATION

This application claims the priority benefit of China application serial no. 201610666231.5, filed on Aug. 12, 2016. The entirety of the above-mentioned patent application is hereby incorporated by reference herein and made a part of this specification.

BACKGROUND OF THE INVENTION

Field of the Invention

The present invention relates to the technical field of pattern recognition and human-computer interaction, and in particular, to a method for implementing a human skeleton tracking system based on depth data.

Description of Related Art

Research on human recognition using depth images is a popular topic in the current field of computer vision. The content of the research on human recognition using depth images covers human detection and tracking, gesture recognition, movement recognition, face recognition, gender recognition, behavior and event recognition, and the like. Methods of the research on human recognition using depth images involve nearly all pattern recognition theories and techniques, for example, statistical theory, transformation theory, context dependence, classification and clustering, machine learning, template matching, and filtering. Human recognition using depth images has very high application value. Within a particular space range, depth images may be used to perform recognition in a 3D space, so as to replace the binocular vision of a visible-light camera. For example, human recognition using depth images is applied to a safety monitoring system in a public place such as an airport or a subway or in a criminal investigation; or is applied to access control systems, games, and the like with human-computer interaction; or is applied to sports matches or videos for capture and analysis of movement details.

Chinese Patent Application 201110160313.X discloses a "METHOD AND SYSTEM FOR RECOGNIZING LIMB MOVEMENT BASED ON DEPTH IMAGE SENSING." The method includes: acquiring depth image information of a user and an environment where the user is located; extracting a limb contour of the user from a background of the depth image information; respectively changing the sizes of different parts in a standard human skeletal framework to adapt to the limb contour of the user, obtaining an adapted limb skeletal framework of the user; in the depth image information, tracking and extracting data which represents the movement of the limbs of the user in a manner adapted to the body skeletal framework; and recognizing a limb movement of the user according to the data which represents the movement of the limbs of the user. However, the method suffers from obvious deficiencies in extracting a limb contour from a depth image and registering with a stored human skeletal framework. First, a human skeletal framework needs to be acquired in advance in the method. Second, during registration and adaptation of a human skeletal framework and a limb contour, the sizes of different parts in the skeletal framework may be changed to adapt to the limb contour; however, persons have various body sizes and a same person has various gestures, resulting in various shapes of limb contour, so that it is very difficult to adapt the skeletal framework to the limb contour. Third, for various human limb contours, a massive amount of data of skeletal frameworks needs to be acquired in advance, which is difficult to implement.

Chinese Patent Application 201310327955.3 discloses a "MAN-COMPUTER INTERACTION METHOD FOR AN INTELLIGENT HUMAN SKELETON TRACKING CONTROL ROBOT ON THE BASIS OF KINECT." The method includes: detecting, by a 3D depth sensor, actions of an operator to obtain data frames, converting the data frames into an image, segmenting an object similar to a human body in the image and a background environment, and obtaining depth-of-field data; extracting human skeleton information, recognizing different portions of the human body, and establishing a 3D coordinate of joints of the human body; recognizing rotation information of skeleton joints of the two hands of the human body, recognizing, by capturing changes of angles of the different skeleton joints, which hand of the human body is triggered; analyzing different action features of the operator, using corresponding characters as control instructions, which are sent to a robot of a lower computer; and receiving and processing, by an AVR single-chip microcomputer master controller, the characters, and controlling the robot of the lower computer to perform corresponding actions, achieving human-computer interaction of the intelligent human skeleton tracking control robot on the basis of the kinect. However, the method still suffers from obvious deficiencies. First, during the movement of a human body, a self-blockage problem unavoidably occurs for depth-of-field data of a single camera, and for a blocked portion of the human body, depth-of-field data cannot be obtained and thus the position of joints cannot be obtained through matching. Second, persons have various body sizes and garments, and even for a same person, a same human body portion may be different in shape in various gestures, so that an accurate matching result cannot be obtained.

Chinese Patent Application 201010101562.7 discloses a "METHOD FOR TRACKING HUMAN SKELETON MOTION IN UNMARKED MONOCULAR VIDEO." The method includes the following steps: (1) preprocessing a video image to obtain a binary image with a background and a human body separated from each other; (2) performing distance transformation on the binary image to obtain a geometric skeleton; (3) processing the geometric skeleton to find endpoints and inflections as key points of the geometric skeleton; (4) marking the key points with semantics of human joints in the geometric skeleton according to relative positional relationships of human joints in a preset human skeleton model; (5) adopting a method integrating sparse features and optical flow tracking to find a corresponding matching point in a subsequent frame for each point which is successfully marked as a human joint; and (6) adopting a particle filtering method to estimate a possible state of a failure part in the tracking results, and recovering the tracking process. However, the method still suffers from obvious deficiencies in obtaining a skeleton. First, the skeleton extracted in the method is a 2D skeleton and does not include depth information. Second, the accuracy is not high in extracting a skeleton in different gestures based on a color image.

In conclusion, how to overcome the deficiencies in the prior art has become one of the key problems that urgently need to be solved in the current technical field of pattern recognition and human-computer interaction.

SUMMARY OF THE INVENTION

The present invention provides a method for implementing a human skeleton tracking system based on depth data to overcome the deficiencies in the prior art. The present invention enables the human skeleton tracking system to effectively resolve problems in conventional interaction styles. The present invention has advantages such as directness in control, visualization, portability, and low costs.

A method for implementing a human skeleton tracking system based on depth data according to the present invention is characterized in that, the method is specifically applied to a human skeleton tracking system based on depth data which is composed of a data acquisition unit, a limb segmentation unit, a skeleton point unit, and a tracking display unit. The units are in a relationship of sequential invocation. The limb segmentation unit uses scene depth data obtained after processing by the data acquisition unit to perform limb segmentation. The skeleton point unit uses the result obtained after segmentation by the limb segmentation unit to compute specific positions of respective skeleton points of a limb. The tracking display unit uses the positions of the skeleton points computed by the skeleton point unit to establish a skeleton model of the human body and perform tracking display. Specific steps of the method include:

Step 1: acquiring depth data of a human body by a depth sensor;

Step 2: voxelizing the acquired depth data, and performing downsampling;

Step 3: removing a background and separating a human body from a scene;

Step 4: selecting a proper proportion to establish a bounding box in the human body while ensuring that two vertices at the top of the bounding box are located within the human body region;

Step 5: distinguishing the head, the left hand, the right hand, and the two feet of the human body by using the bounding box;

Step 6: using a seed point growing algorithm to calculate depth information of a maximum block in the bounding box to serve as an average depth value of the entire bounding box, marking the hands in the bounding box using the average depth value, and setting the remaining human body parts to a background color;

Step 7: performing further region growing of seed points, isolating the hands from the head by a method of establishing shoulder circular bounding boxes, and setting other portions of the human body to a background color using the same method, leaving only the head and the two hands;

Step 8: computing the center of mass of each small block obtained by segmenting the hand and respectively setting all small blocks in a region 1 and a region 2 to a same color using the centers of mass;

Step 9: establishing a region 3 and a region 4 from a vertex 1 and a vertex 2 and associating the shoulders with the respective left and right hands;

Step 10: establishing a search region 5 below the shoulders and associating a small block obtained through segmentation with a big block which has the closest relation to the small block;

Step 11: finding the head region by using the depth information and setting the head region to a fixed color;

Step 12: dividing the image into a left region and a right region by making a centerline of the bounding box and distinguishing between the left hand and the right hand by using respective percentages of the left hand in the left region and the right hand in the right region;

Step 13: calculating limb means of the left hand and the right hand as elbow joints of the left hand and the right hand respectively and finding arm endpoints corresponding to the left hand and the right hand by determining respective anchors; and Step 14: connecting all endpoints of the head, shoulders, hips, and arms, establishing a human skeleton model, and performing tracking display.

Further preferred solutions of the method for implementing a human skeleton tracking system based on depth data of the present invention is as follows.

The data acquisition unit is configured to use a depth camera Kinect to acquire depth data of a scene and establish a three-dimensional coordinate system, where a Z coordinate denotes a depth value of each pixel point. The data acquisition unit is configured as an input part of the present invention to use a depth camera capable of capturing depth information of a scene to capture a video sequence which carries depth information, including time of flight, structured light, three-dimensional image, and the like. The depth information may include a depth value of each pixel point of a human body. A 3D spatial region may be reconstructed over a range by using a depth image. Even if there is a blocked part between two human bodies, a distance difference is generated in a depth image because of a longitudinal relationship of the human bodies, that is, grayscale values are layered. Therefore, a threshold may be used to segment a blocked human body or different blocked parts of a same human body, so as to resolve to a certain extent a problem in which a human body is blocked or different parts of a same human body overlap.

The limb segmentation unit is configured to establish, according to an acquired depth image of a human body, a bounding box in the human body by using depth data information, to perform segmentation by using a seed point growing algorithm, and to combine small blocks obtained through segmentation for several regions, so as to achieve recognition of several major portions of the human body. The limb segmentation refers to distinguishing among the head, hands and feet of the human body. A bounding box is established by using the acquired depth image. A series of operations such as a seed point region growing algorithm, segmentation, and region combination are used to separate the head, hands, and feet of the human body, and to further specifically distinguish between the left hand and the right hand.

The skeleton point unit is configured to establish human portions separated through limb segmentation, and to determine skeleton joints of the head, center of mass, shoulders, hips, legs, arms, hands, elbows, and knees of the human body using depth information of limbs by a center of mass method. The skeleton point unit determines portions of the human body through limb segmentation. By using a series of operations such as establishment of anchors on the depth information and matching of actions and gestures per regions, skeleton joints of portions of the human body are determined.

The tracking display unit is configured to connect the established skeleton joints of a human body to form a skeleton model of the human body which can track, when the human body makes a series of movements, corresponding movements of the human body, and to display tracking of the movements by the skeleton model. The tracking display unit establishes a skeleton tracking model of a human body by connecting the established skeleton joints, so as to achieve tracking display of a limb movement of the human body.

As compared with the prior art, the present invention has a significant advantage in that the present invention provides a method for implementing a human skeleton tracking system based on depth data, which has advantages such as directness in control, visualization, portability, and low costs. In the present invention, depth information of a human body acquired by a depth camera is used, a rectangular bounding box and a circular bounding box are established in the human body, seed point region growing is used to achieve segmentation of human body portions, a big region which has the closest relation to a small region obtained through segmentation is found to perform combination so as to achieve segmentation of the limbs of the human body, anchors are established by using the limbs obtained through segmentation, and a movement gesture of an object is matched per regions, so as to establish a human skeleton tracking system. The present invention can achieve an effect of real-time tracking and presentation of a human skeleton and ensure the user experience in operation, and can also reduce early investment costs and later maintenance costs of the human skeleton tracking system.

DETAILED DESCRIPTION OF THE INVENTION

Figures 1, 2:
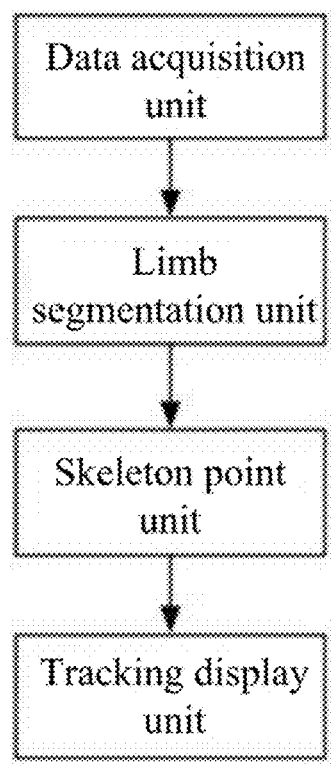
FIG. 1 is a schematic diagram of sequential invocation of units in a method for implementing a human skeleton tracking system based on depth data according to the present invention.
FIG. 2 is a schematic diagram of a depth value of each pixel point of a depth image of a scene, acquired by a depth camera.

Specific implementations of the present invention are further described below in detail with reference to the accompanying drawings and embodiments.

A method for implementing a human skeleton tracking system based on depth data according to the present invention is specifically applied to a human skeleton tracking system based on depth data which is composed of a data acquisition unit, a limb segmentation unit, a skeleton point unit, and a tracking display unit. The units are in a relationship of sequential invocation. The limb segmentation unit uses scene depth data obtained after processing by the data acquisition unit to perform limb segmentation. The skeleton point unit uses the result obtained after segmentation by the limb segmentation unit to compute specific positions of respective skeleton points of a limb. The tracking display unit uses the positions of the skeleton points computed by the skeleton point unit to establish a skeleton model of the human body and perform tracking display. Specific steps of the method include:

Step 1: acquiring depth data of a human body by a depth sensor;

Step 2: voxelizing the acquired depth data and performing downsampling;

Step 3: removing a background and separating a human body from a scene;

Step 4: selecting a proper proportion to establish a bounding box in the human body while ensuring that two vertices at the top of the bounding box are located within the human body region;

Step 5: distinguishing the head, the left hand, the right hand, and the two feet of the human body by using the bounding box;

Step 6: using a seed point growing algorithm to calculate depth information of a maximum block in the bounding box to serve as an average depth value of the entire bounding box, marking the hands in the bounding box using the average depth value, and setting the remaining human body parts to a background color;

Step 7: performing further region growing of seed points, isolating the hands from the head by a method of establishing shoulder circular bounding boxes, and setting other portions of the human body to a background color using the same method, leaving only the head and the two hands;

Step 8: computing the center of mass of each small block obtained by segmenting the hand and respectively setting all small blocks in a region 1 and a region 2 to a same color using the centers of mass;

Step 9: establishing a region 3 and a region 4 from a vertex 1 and a vertex 2 and associating the shoulders with the respective left and right hands;

Step 10: establishing a search region 5 below the shoulders and associating a small block obtained through segmentation with a big block which has the closest relation to the small block;

Step 11: finding the head region by using the depth information and setting the head region to a fixed color;

Step 12: dividing the image into a left region and a right region by making a centerline of the bounding box and distinguishing between the left hand and the right hand by using respective percentages of the left hand in the left region and the right hand in the right region;

Step 13: calculating limb means of the left hand and the right hand as elbow joints of the left hand and the right hand respectively and finding arm endpoints corresponding to the left hand and the right hand by determining respective anchors; and Step 14: connecting all endpoints of the head, shoulders, hip, and arms, establishing a human skeleton model, and performing tracking display.

Specific embodiments of the method for implementing a human skeleton tracking system based on depth data according to the present invention are disclosed as follows.

The data acquisition unit in the present invention is configured to use a depth camera Kinect to acquire depth data of a scene and establish a three-dimensional coordinate system, where a Z coordinate denotes a depth value of each pixel point. A specific implementation process of the data acquisition unit includes: the depth camera is used to acquire speckle patterns of the scene through a CMOS photosensitive component, and these patterns at different positions are stored as reference images; when an opaque object is placed in the scene or an object moves in the scene, new speckles are formed on the surface of the object, so as to obtain test images, at which speckle patterns are changed and are different from all the reference images; according to a calibration relationship between a selected reference image and a light source, and by using geometric transformation, a distance from the object to the light source is computed, so as to construct a 3D image; the distance data is normalized and transformed into an image grayscale value, and finally, the generated depth image is output to an external processing device; and other operations such as 3×3, 5×5, and 7×7 are performed on the depth image to perform voxelization, so as to achieve downsampling.

The limb segmentation unit in the present invention is configured to establish, according to an acquired depth image of a human body, a bounding box in the human body by using depth data information, to perform segmentation by using a seed point growing algorithm, and to combine small blocks obtained through segmentation for several regions, so as to achieve recognition of several major portions of the human body. A specific implementation process of the limb segmentation includes: determining a proper human body proportion to compute a human torso bounding box. The computation of the human torso bounding box needs to meet a particular constraint. For example, a boundary of the bounding box should be consistent with a human torso as much as possible, and two vertices at the top of the bounding box should be located within the human body region.

After the human torso bounding box is computed, if another portion (i.e. a hand or arm) of the human body exists in front of the human torso, the portion is segmented. A segmentation method is to perform seed point region growing in the human torso bounding box to perform region segmentation, and compute an average depth of each region, where a relatively large average depth is a torso average depth. If the average depth of a region has a relatively large difference from the torso average depth, the region is marked.

After the human torso bounding box is computed, seed point region growing is performed on the human body once, and two circular bounding boxes at the shoulders are established to distinguish between the hand and the head. Also similarly, circular bounding boxes are established in other regions of the human body to first set regions other than the head and the arms of the human body to a color which is the same as that of a background. The rest small impurity points in the regions and noise in a human contour are removed. For a case in which an arm is segmented into several parts, region search blocks of several cases are established. At the same time, particular computation is performed on regions obtained through segmentation in the search blocks, to determine which portions of the human body the regions obtained through segmentation belong to. Eventually, the head is completely distinguished from the left hand and the right hand of the human body.

The skeleton point unit in the present invention is configured to establish human portions separated through limb segmentation, and to determine skeleton joints of the head, center of mass, shoulders, hips, legs, arms, hands, elbows, and knees of the human body using depth information of limbs by a center of mass method. A specific implementation process of establishing a skeleton point includes: the head, the left hand, and the right hand which are obtained through segmentation are used, and information of pixel points is used to compute the center of mass to determine the position of a skeleton point of the head; a rectangular bounding box determined above is used to compute the center of mass, to determine the hips of the human body; two vertices at the top of the rectangular bounding box are used to determine the shoulders of the human body; the centers of mass of the left hand and the right hand are respectively computed to determine the positions of the elbows; an anchor is set and position relationships among the anchor, the elbows, and endpoints of the arms are determined, so as to determine the endpoints of the arms.

The tracking display unit in the present invention is configured to connect the established skeleton joints of a human body to form a skeleton model of the human body which can track, when the human body makes a series of movements, corresponding movements of the human body, and to display tracking of the movements by the skeleton model. A specific implementation process of the tracking display includes: connecting the positions of the skeleton joints computed above to form a preliminary human skeleton model of the human body. After a person makes a particular gesture in front of the depth camera, a tracking model can, according to the generated skeleton joint model, make corresponding limb movements, and display the same.

The specific embodiments of the method for implementing a human skeleton tracking system based on depth data according to the present invention are further described in detail with reference to FIG. 1 to FIG. 18.

FIG. 1 is a schematic diagram of sequential invocation of units in a method for implementing a human skeleton tracking system based on depth data. The method for implementing a human skeleton tracking system based on depth data of the present invention is specifically applied to a human skeleton tracking system based on depth data which is composed of a data acquisition unit, a limb segmentation unit, a skeleton point unit, and a tracking display unit. The units are in a relationship of sequential invocation. The limb segmentation unit uses scene depth data obtained after processing by the data acquisition unit to perform limb segmentation. The skeleton point unit uses the result obtained after segmentation by the limb segmentation unit to compute specific positions of respective skeleton points of a limb. The tracking display unit uses the positions of the skeleton points computed by the skeleton point unit to establish a skeleton model of the human body and perform tracking display.

FIG. 2 is a schematic diagram of a depth value of each pixel point of a depth image of a scene, acquired by a depth camera. The depth image includes a two-dimensional (2D) pixel region of a captured scene. Each pixel in the 2D pixel region may represent a depth value, for example, a length or a distance in centimeter, millimeter or the like which is from an object in a captured scene to a capturing device.

A grid with one or more voxels is generated based on the received depth image. Information included in the received depth image may be used to generate one or more voxels, so as to perform downsampling on the received depth image, such that a downsampled depth image may be generated.

The depth image may be divided into individual pixel parts or pixel blocks, for example, 2×2, 3×3, 4×4, and 5×5. Each part or block may be processed to generate a voxel of the depth image. The voxel may represent a spatial orientation of the 2D depth image in the real world. The orientation of each voxel may be based on an effective value in a block or some pixels represented by the voxel, an average depth value of a non-zero depth value, a maximum value or minimum value of the voxel block, or any other suitable information.

Figure 3:
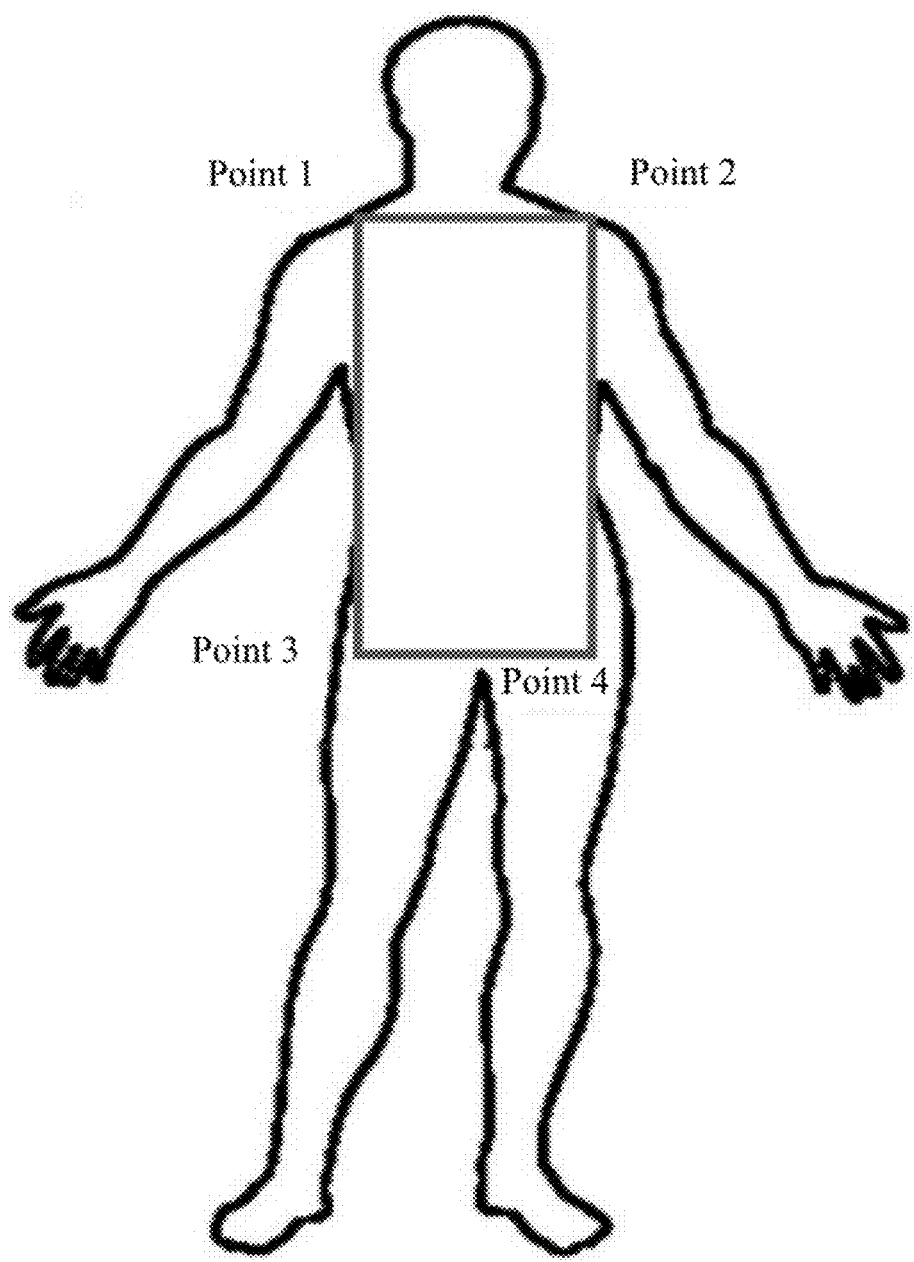
FIG. 3 is a schematic diagram of a bounding box in a human body, established using an acquired depth image.

FIG. 3 is a schematic diagram of a bounding box in a human body, established using an acquired depth image. To distinguish among the head, hands, and feet of a human body, percentages of an uppermost portion, a lowermost portion, a leftmost portion, and a rightmost portion in the human body are computed to determine the bounding box of the human body. During computation of the top of the bounding box, it should also be noted that a point 1 and a point 2 of the bounding box which are determined by using the top of the bounding box and the left and right ends of the bounding box are required to be located within the human body. By means of the bounding box in the human body, the head, the left hand, the right hand, and the feet of the human body may be approximately distinguished.

Figure 4:
FIG. 4 is a schematic diagram of a background color of marking pixels in a bounding box.

FIG. 4 is a schematic diagram of a background color of marking pixels in a bounding box. Aside from depth information of pixel points of the human body which are in the bounding box, the pixel points in the entire bounding box are all marked with a background color. In this way, only the head, the left hand, the right hand, and the feet of the human are left.

Figure 5:
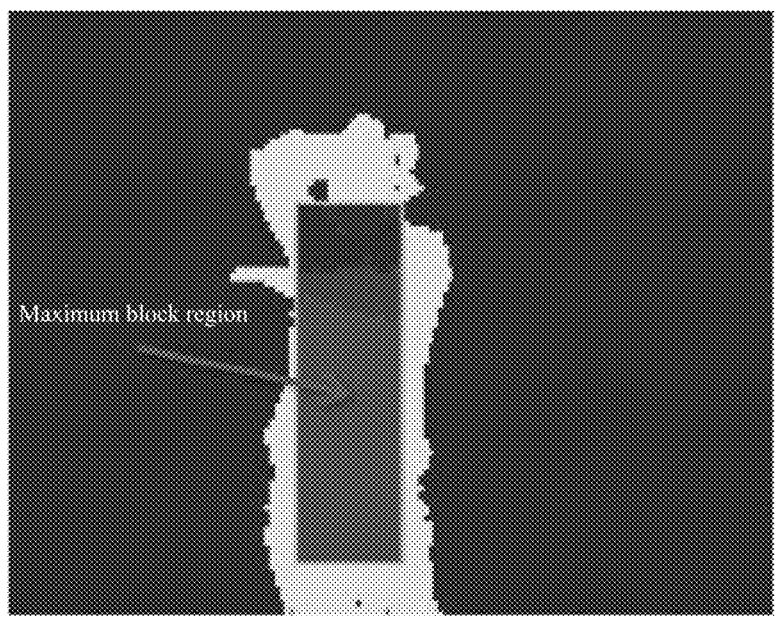
FIG. 5 is a schematic diagram of selecting an average depth value of a maximum region in a bounding box as a depth value of the bounding box.

FIG. 5 is a schematic diagram of selecting an average depth value of a maximum region in a bounding box as a depth value of the bounding box. FIG. 5 shows that a hand which moves into the region in the bounding box is marked, seed point region growing is performed on the region in the bounding box, and segmentation and marking are performed again. When the hand moves out of the bounding box, a maximum block region in the bounding box is the human body part. When the hand moves into the bounding box, a maximum block region in the bounding box is also the human body part. When the hand moves in the bounding box, the depth value of the hand is less than the depth value of the body part. Therefore, at this time, a depth average value of a maximum block obtained through segmentation in the bounding box is calculated as the depth average value of the entire bounding box. By using the depth average value of a hand region in the bounding box being less than the depth average value (an average value of the maximum block) of the bounding box, a proper threshold is selected to separately mark the hand with a color in the bounding box, and the human body part in the bounding box is marked with a background color.

Figure 6:
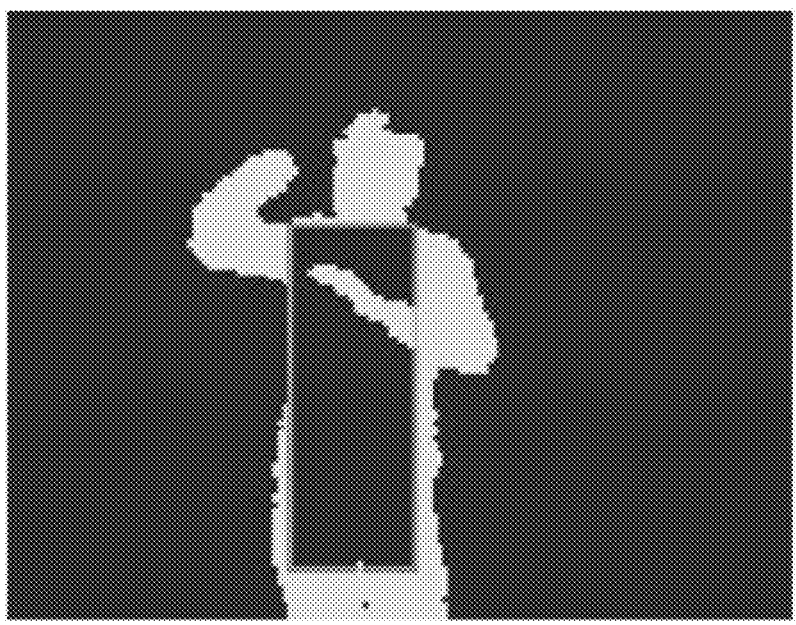
FIG. 6 is a schematic diagram of separately marking a hand when the hand moves in a bounding box.

FIG. 6 is a schematic diagram of separately marking a hand when the hand moves in a bounding box. FIG. 6 shows that when the hand moves in a region in the bounding box, the hand is separately marked, and the human body portion in the bounding box is not marked. In this way, researches on limb portions of the human body may be facilitated, without considering the depth of other portions of the human body.

Figure 7:
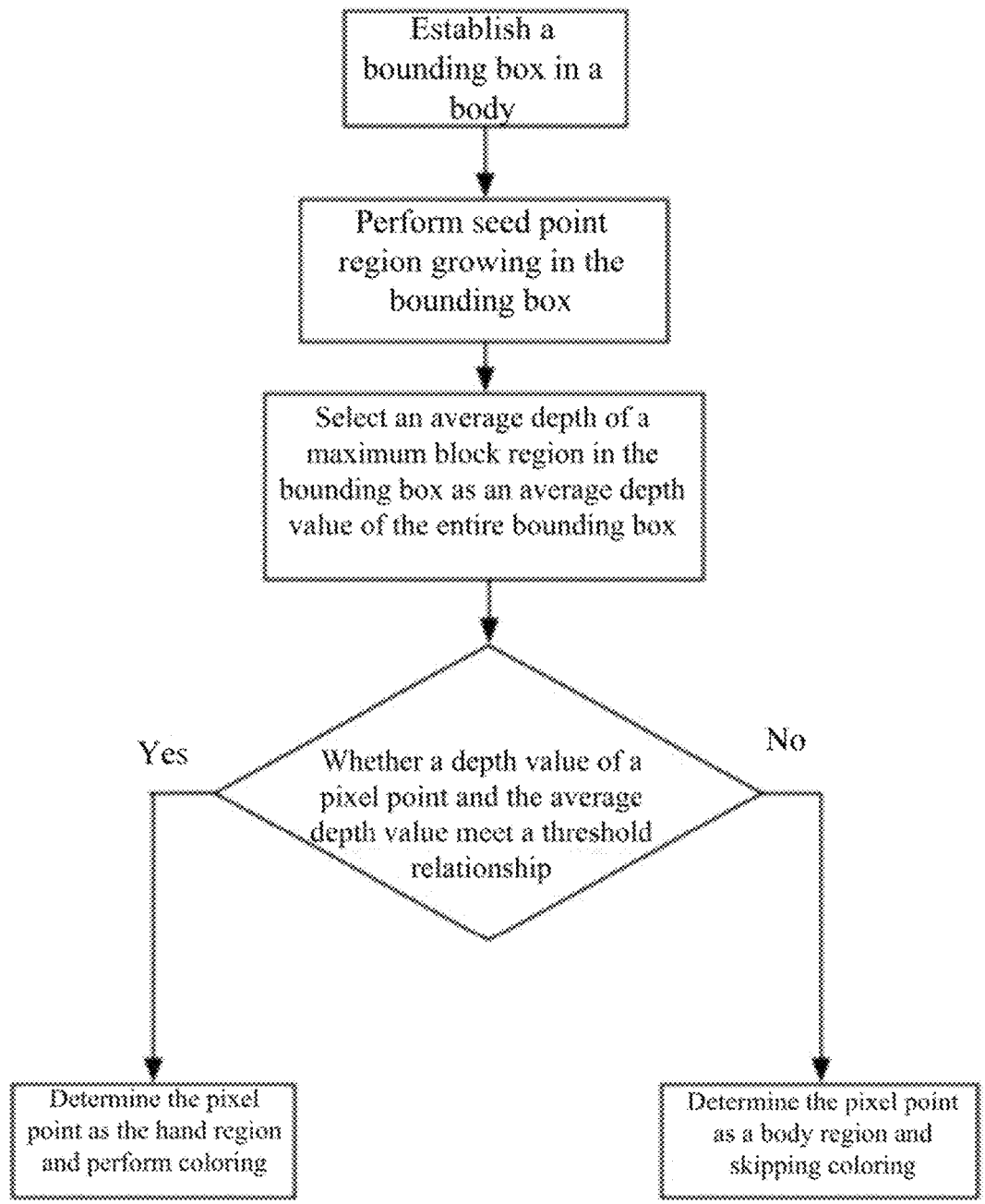
FIG. 7 is a schematic flowchart of marking a hand in a bounding box.

FIG. 7 is a schematic flowchart of marking a hand in a bounding box. FIG. 7 is a schematic flowchart of coloring a hand region in the bounding box. A bounding box in a body is established by using a depth image acquired by a data acquisition unit. Seed point region growing is performed in the bounding box to perform region segmentation. An average depth of a maximum block region in the bounding box is selected as an average depth value of the entire bounding box. Comparison is performed to find whether a depth value of each pixel point in the bounding box and the average depth value meet a threshold relationship; if so, the pixel point is determined as the hand region and coloring is performed; otherwise, the pixel point is determined as a body region and coloring is skipped.

Figure 8:
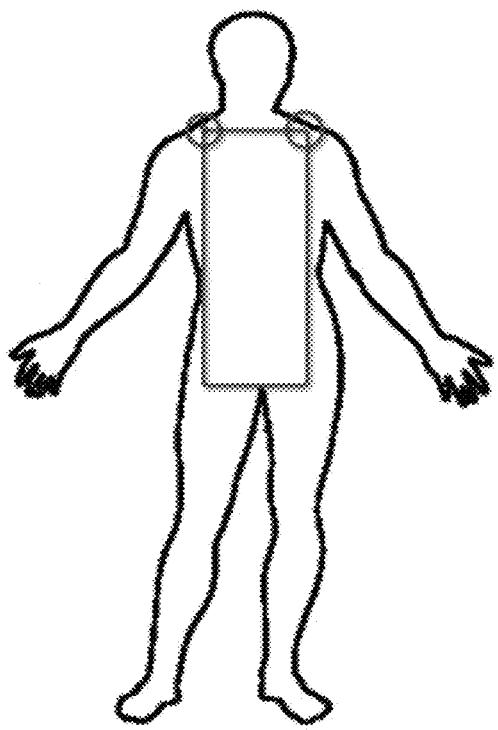
FIG. 8 is a schematic diagram of establishing a circular bounding box at a shoulder.

FIG. 8 is a schematic diagram of establishing a circular bounding box at a shoulder. FIG. 8 shows that to distinguish among the head and the left and right hands of a human body more accurately, two circular bounding boxes similar to a rectangular bounding box in a human body are established at a point 1 and a point 2 of the bounding box. The two bounding boxes are used to isolate the left and right hands from the head.

Figure 9:
FIG. 9 is a schematic diagram of human depth after a circular bounding box is established and noise is removed.

FIG. 9 is a schematic diagram of human depth after a circular bounding box is established and noise is removed. Similarly, some other circular bounding boxes are established on a left side and a right side of the bounding box to set regions at two sides of the human body and the feet to a background color. After the regions at the two sides of the human body and the regions of the feet are removed, impurity points in some small regions still affect subsequent color marking of the left and right hands and the head. At the same time, there are some noise at boundaries of the hand regions and the head region. When a counted number of times in which a color appears is less than a threshold, the color is marked as a background color. The result is shown in FIG. 9.

Further, during seed point region growing, the hand is segmented into several parts. When the hand moves to block the head, the head is also segmented into two regions. To acquire the complete and continuous left hand, right hand, and head, the image is segmented into suitable regions, and it is observed whether there is a small block in a region to be combined into a big block region; if so, a proper scheme is selected and the small block region is combined into the big block region.

Figure 10:
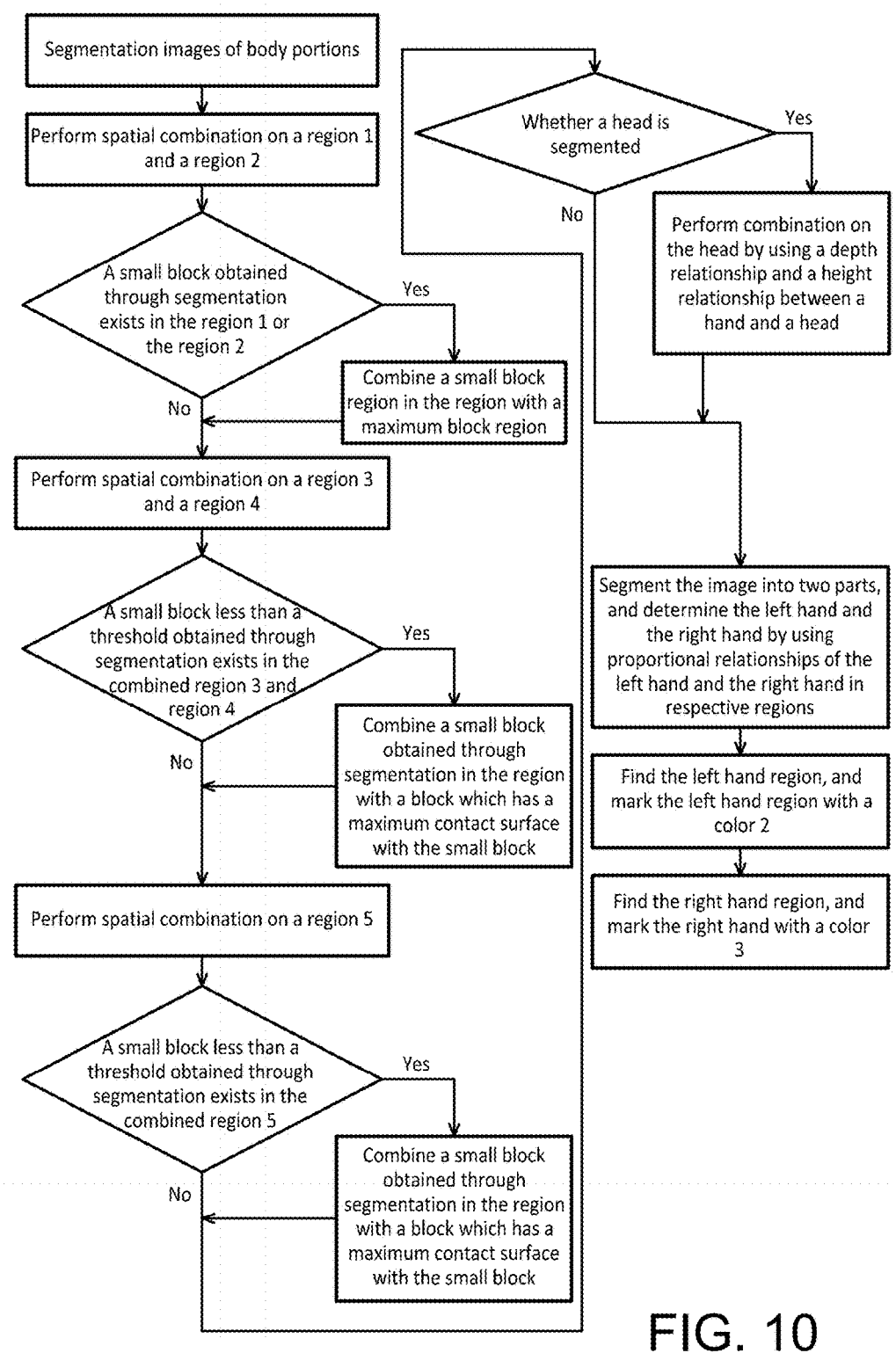
FIG. 10 is a schematic flowchart of combining regions obtained through segmentation.

FIG. 10 is a schematic flowchart of combining regions obtained through segmentation. FIG. 10 is a schematic flowchart of combining small block regions which are obtained through segmentation. Spatial combination is performed on a region 1 and a region 2 on acquired segmentation images of body portions. It is determined whether the center of mass of a small block obtained through segmentation exists in the region 1 or the region 2; if so, a small block region in the region is combined with a maximum block region; otherwise, spatial combination is performed on a region 3 and a region 4. It is determined whether a small block obtained through segmentation less than a threshold exists in the combined region 3 and region 4; if so, a small block region in the region is combined with the maximum block region; otherwise, it is further determined to perform spatial combination on a region 5. If a small block less than a threshold exists in the combined region 5, a small block obtained through segmentation in the region is combined with a block which has a maximum contact surface with the small block; otherwise, it is determined whether the head is segmented. If the head is segmented, a depth relationship and a height relationship between a hand and a head are used to perform combination on the head. If the head is not segmented, the image is segmented into two parts, and proportional relationships of the left hand and the right hand in respective regions are used to determine the left hand and the right hand. The left hand region is found, and the left hand region is marked with a color 2. The right hand region is found, and the right hand is marked with a color 3.

Figure 11:
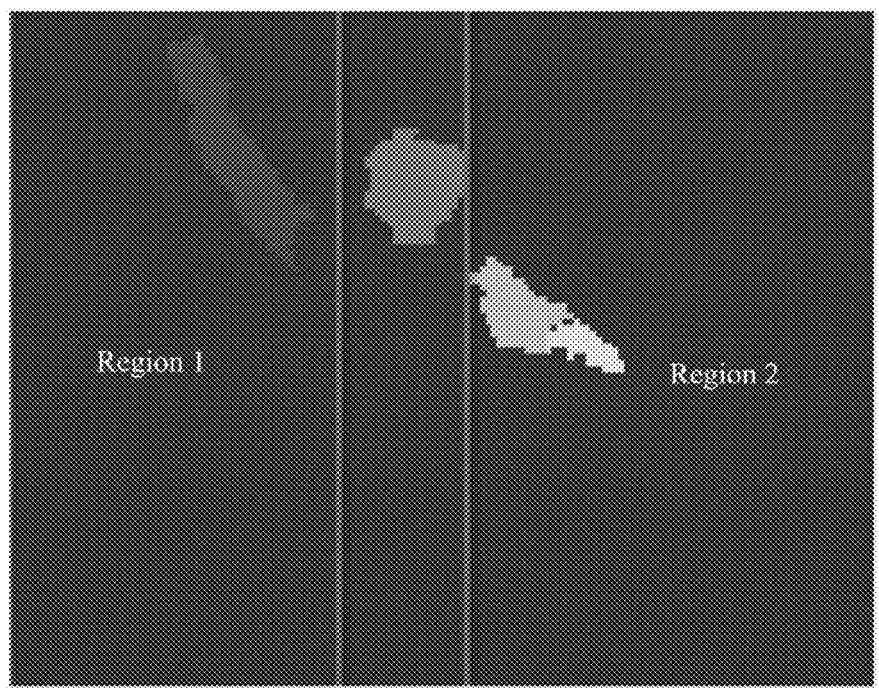
FIG. 11 is a schematic diagram of a region 1 and a region 2.

FIG. 11 is a schematic diagram of a region 1 and a region 2. FIG. 11 shows computation of the center of mass of each color block by using X, Y, and a depth value. Next, all color blocks having centers of mass in the region 1 or all color blocks having centers of mass in the region 2 are found. If more than one color block region exists in the region 1 or the region 2, all regions smaller than a maximum color block are selected from the regions, and all the regions smaller than the maximum color block are marked with the color of the maximum color block.

Figure 12:
FIG. 12 is a schematic diagram of a region 3 and a region 4.

FIG. 12 is a schematic diagram of a region 3 and a region 4. FIG. 12 shows a case in which a shoulder and a hand cannot be combined because the centers of mass of the shoulder and the hand are respectively located inside and outside a bounding box. A region 3 is established from the point 1 of the bounding box to the lower left corner, and a region 4 is established from the point 2 of the bounding box to the lower right corner. Small regions having a region size less than a threshold are found in the region 3 and the region 4 respectively. When a color block which meets the threshold appears, it is determined whether other color blocks greater than the threshold exists in this region; if so, the color block less than the threshold is marked with a color of a maximum block in a same search block.

Figure 13:
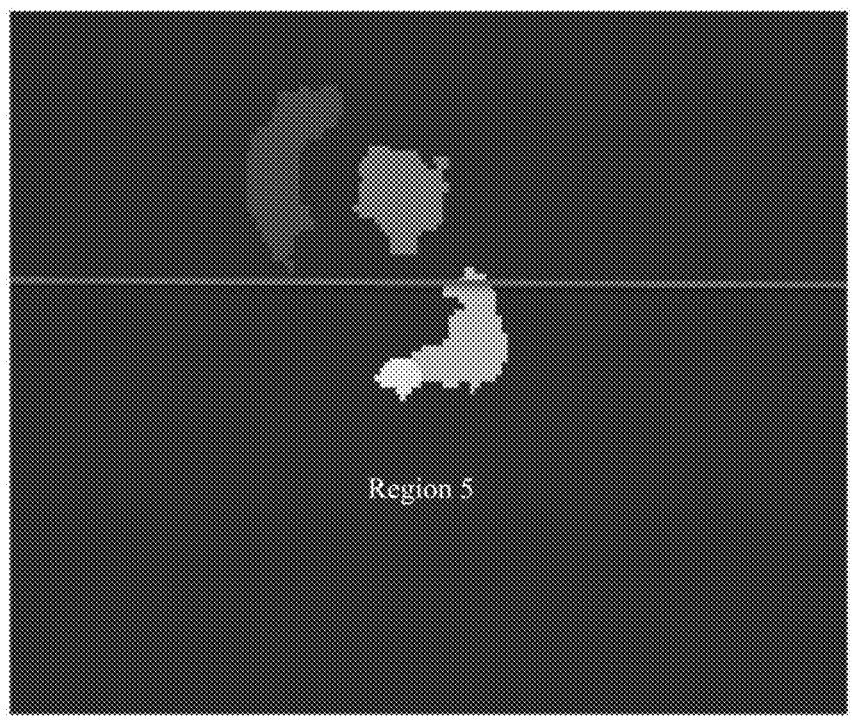
FIG. 13 is a schematic diagram of a region 5.

FIG. 13 is a schematic diagram of a region 5. FIG. 13 shows that when the center of mass of a small block obtained through segmentation is located inside a bounding box rather than outside the bounding box at this time, the small block cannot be combined with a big block having a center of mass outside the bounding box. As a result, the hand is segmented. A region 5 from the top of the bounding box downwards is established. For a small block obtained through segmentation in the bounding box, an uppermost end, a lowermost end, a leftmost end, and a rightmost end of the small block are calculated. A search from top to bottom and from left to right is made for another color block which has the closest relation to the small block, and the small block obtained through segmentation is marked with a color of the color block which has the closest relation to the small block, so as to combine small blocks obtained through segmentation in a rectangular bounding box.

Figure 14:
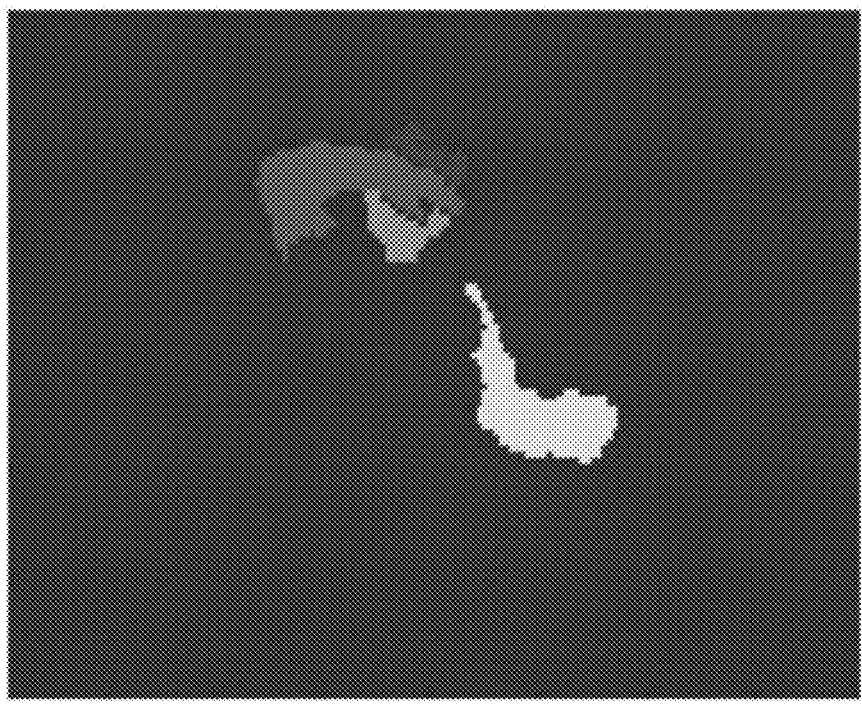
FIG. 14 is a schematic diagram of segmentation of the head.

FIG. 14 is a schematic diagram of segmentation of the head. FIG. 14 shows a case in which when a hand moves to block the head, the head is segmented into two parts.

Figure 15:
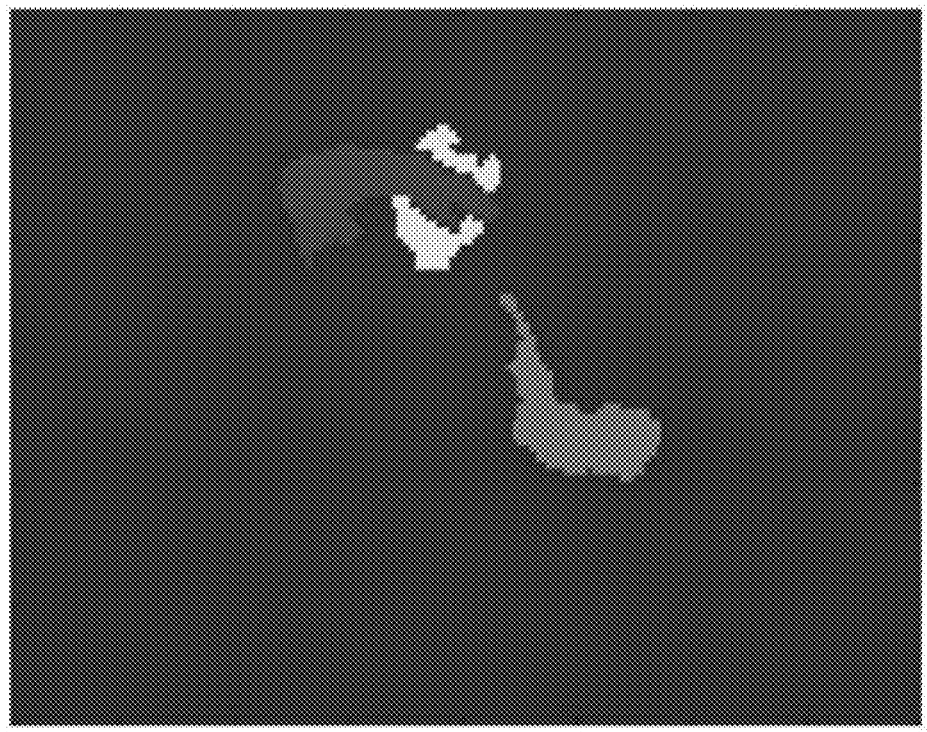
FIG. 15 is a schematic diagram of combination of the head.

FIG. 15 is a schematic diagram of combination of the head. FIG. 15 shows that during calibration of the head, a depth value of the head is usually greater than a depth value of a hand. In some special cases, when the depth value of the hand is greater than the depth value of the head, it is considered to compare the height of the head with the height of the hand to distinguish between the head and the hand. When the head is segmented into two parts, the two parts are regions having relatively large depth values in an image. However, when the hands are crossed in front of the chest, the hands are also segmented into two parts. To distinguish whether the head or the hands are segmented into two parts, the head which is segmented into two parts is found according to the conditions that the two parts of the head being segmented have relatively large depth values and a difference between the depth values of the two parts is less than a threshold.

Figure 16:
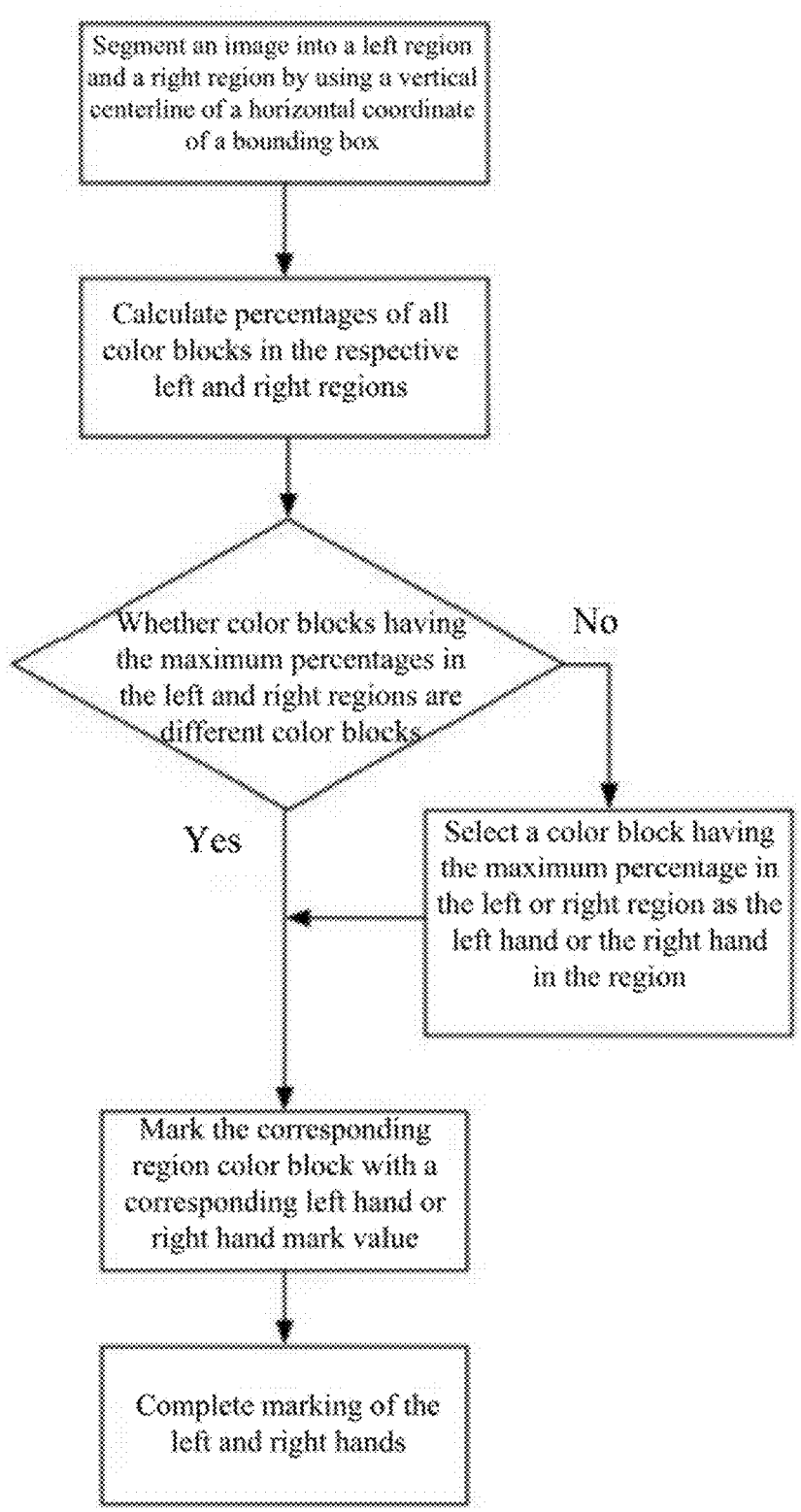
FIG. 16 is a schematic flowchart of distinguishing between the left hand and the right hand.

FIG. 16 is a schematic flowchart of distinguishing between the left hand and the right hand. FIG. 16 is a flowchart of distinguishing, when a hand moves, which color block belongs to the left hand and which color block belongs to the right hand, and marking the found color block of the left hand with a fixed color and the found color block of the right hand with another fixed color. A vertical centerline of a horizontal coordinate of a bounding box is used to segment an image into a left region and a right region. Color blocks of the head and the background color are removed. Percentages of all color blocks in the respective left and right regions are calculated. It is determined whether color blocks having the maximum percentages in the left and right regions are different color blocks. At this time, if a color block only appears in the left region or the right region, the corresponding region color block is marked with a corresponding left hand mark value or right hand mark value.

If two color blocks exist in both the left region and the right region, a color block having a larger percentage in the left or right region is selected as the left hand or the right hand in the region. In this case, if the larger block in the left region and the larger block in the right region are not a same block, the larger blocks in respective regions are marked with a corresponding left hand color value or right hand color value. If the larger block in the left region and the larger block in the right region are the same color block, the percentage of the larger block in the left region is compared with the percentage of the larger block in the right region. One block with the larger value is used as the left hand or right hand in the corresponding region. The other color block is the hand other than the marked hand. Therefore, the left hand and the right hand are calibrated, completing marking of the left and right hands.

To establish a skeleton of a human body, a central point of a rectangular bounding box is selected as the hip, the point 1 and the point 2 of the bounding box are used as a shoulder point 1 and a shoulder point 2 of the human body, the center of mass of the head which is computed from the head region is used as the skeleton point of the head. At the same time, central positions of limb means of the left hand and the right hand are computed as the joint positions of the elbows.

Figure 17:
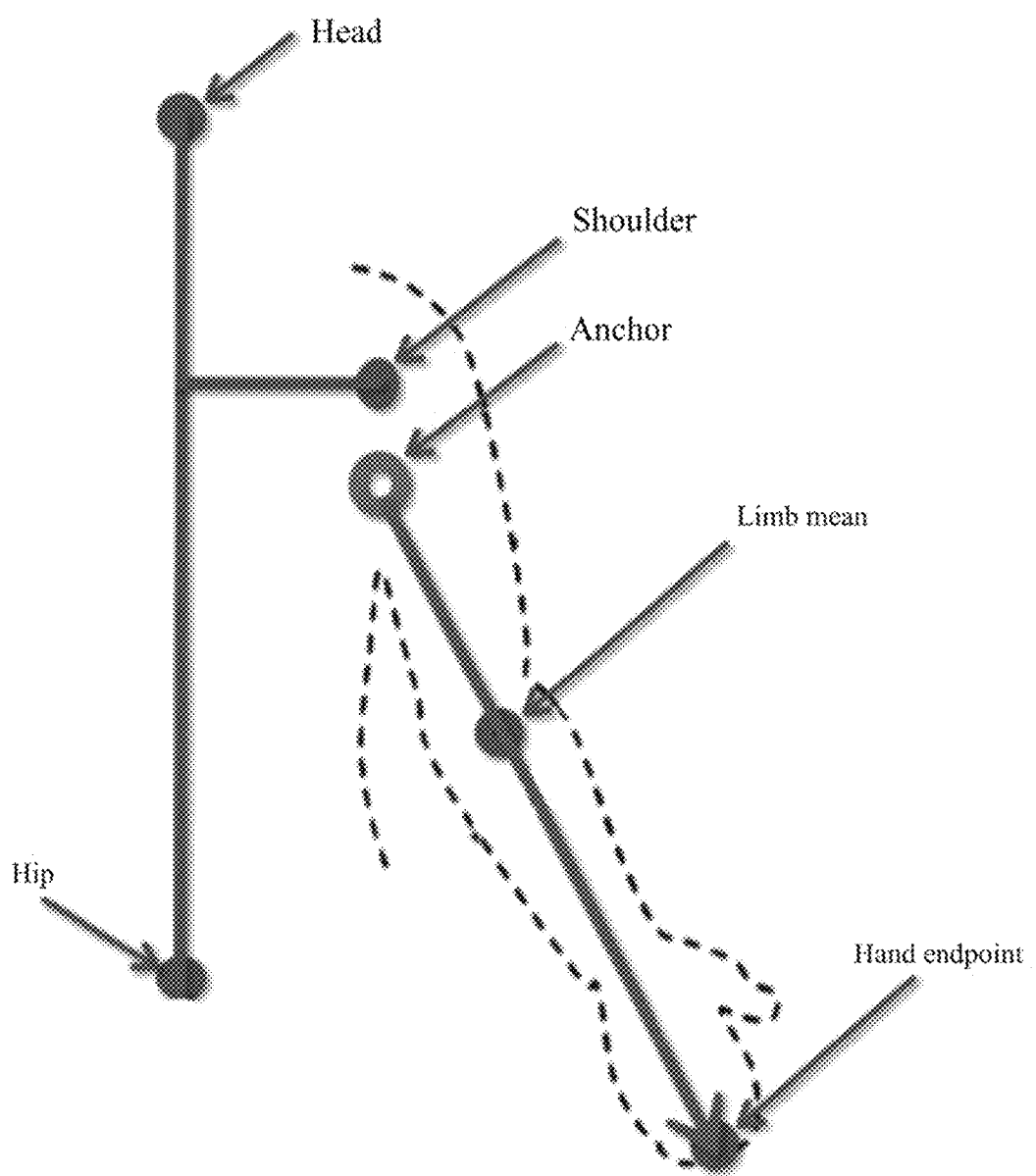
FIG. 17 is a schematic diagram of an anchor movement 1.
Figure 18:
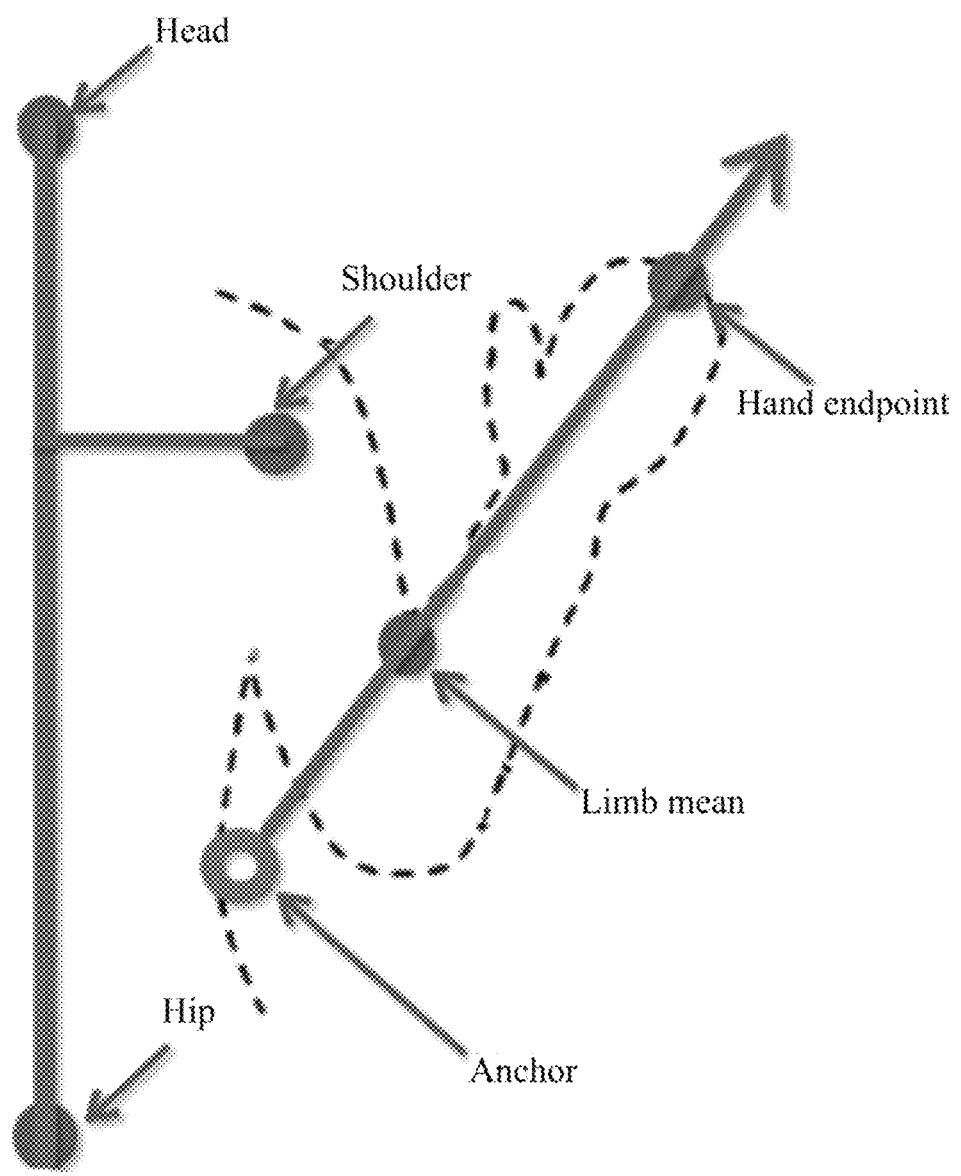
FIG. 18 is a schematic diagram of an anchor movement 2.

FIG. 17 is a schematic diagram of an anchor movement 1. FIG. 18 is a schematic diagram of an anchor movement 2. FIG. 17 and FIG. 18 respectively show that a hand endpoint 1 and a hand endpoint 2 (i.e., limb end skeleton points of hands) are acquired by establishing two anchors. Two anchors (an anchor 1 and an anchor 2) are found in a same direction of shoulder points. When an arm of a person normally swings down, a connecting line passing through an anchor and a limb mean should pass through a hand endpoint corresponding to the connecting line. In this case, the anchor should be located above the limb mean. When a hand of the person gradually rises, the limb mean of the hand also moves upwards. To keep that the connecting line passing through the anchor and the limb mean always passes through the hand endpoint, in this case, the anchor should move downwards as the limb mean moves upwards. A central connecting line of the anchor and the limb mean of the hand is used to determine the hand endpoint.

The contents not specifically described in the detailed description of the present invention are known in the art and may be implemented with reference to known techniques.

The present invention has been verified via repeated tests, and satisfactory test results are achieved.

The foregoing specific implementations and embodiments are used to provide specific support for the technical concept of a method for implementing a human skeleton tracking system based on depth data according to the present invention, and are not intended to limit the protection scope of the present invention. Any equivalent change or equivalent variation made to the technical solutions according to the technical concept of the present invention still falls within the protection scope of the technical solution of the present invention.

What is claimed is:

1. A method for implementing a human skeleton tracking system based on depth data, the method is applied to a human skeleton tracking system based on depth data which is composed of a data acquisition unit, a limb segmentation unit, a skeleton point unit, and a tracking display unit, the units are in a relationship of sequential invocation, the limb segmentation unit uses scene depth data obtained after processing by the data acquisition unit to perform limb segmentation, the skeleton point unit uses the result obtained after segmentation by the limb segmentation unit to compute specific positions of respective skeleton points of a limb, the tracking display unit uses the positions of the skeleton points computed by the skeleton point unit to establish a skeleton model of the human body and perform tracking display, wherein the method comprises:

Step 1: acquiring depth data of a human body by a depth sensor;

Step 2: voxelizing the acquired depth data and performing downsampling;

Step 3: removing a background and separating a human body from a scene;

Step 4: selecting a proper proportion to establish a bounding box in the human body while ensuring that two vertices at the top of the bounding box are located within the human body region;

Step 5: distinguishing a head, a left hand, a right hand, and two feet of the human body by using the bounding box;

Step 6: using a seed point growing algorithm to calculate depth information of a maximum block in the bounding box to serve as an average depth value of the entire bounding box, marking the hands in the bounding box using the average depth value, and setting the remaining human body parts to a background color;

Step 7: performing further region growing of seed points, isolating the hands from the head by a method of establishing shoulder circular bounding boxes, and setting other portions of the human body to a background color using the same method, leaving only the head and the two hands;

Step 8: computing a center of mass of each small block obtained by segmenting the hand and respectively setting all small blocks in a region 1 and a region 2 to a same color using the centers of mass;

Step 9: establishing a region 3 and a region 4 from a vertex 1 and a vertex 2 and associating shoulders with the respective left and right hands;

Step 10: establishing a search region 5 below the shoulders and associating a small block obtained through segmentation with a big block which has the closest relation to the small block;

Step 11: finding a head region by using the depth information and setting the head region to a fixed color;

Step 12: dividing an image into a left region and a right region by making a centerline of the bounding box and distinguishing between the left hand and the right hand by using respective percentages of the left hand in the left region and the right hand in the right region;

Step 13: calculating limb means of the left hand and the right hand as elbow joints of the left hand and the right hand respectively and finding arm endpoints corresponding to the left hand and the right hand by determining respective anchors; and Step 14: connecting all endpoints of the head, shoulders, hip, and arms, establishing a human skeleton model, and performing tracking display.

2. The method for implementing a human skeleton tracking system based on depth data according to claim 1, wherein the data acquisition unit is configured to use a depth camera Kinect to acquire depth data of a scene and establish a three-dimensional coordinate system, where a Z coordinate denotes a depth value of each pixel point.

3. The method for implementing a human skeleton tracking system based on depth data according to claim 2, wherein the limb segmentation unit is configured to establish, according to an acquired depth image of the human body, the bounding box in the human body by using depth data information, to perform segmentation by using the seed point growing algorithm, and to combine small blocks obtained through segmentation for several regions, so as to achieve recognition of several major portions of the human body.

4. The method for implementing a human skeleton tracking system based on depth data according to claim 3, wherein the skeleton point unit is configured to establish human portions separated through limb segmentation, and to determine skeleton joints of the head, center of mass, shoulders, hips, legs, arms, hands, elbows, and knees of the human body using the depth information of limbs by a center of mass method.

5. The method for implementing a human skeleton tracking system based on depth data according to claim 4, wherein the tracking display unit is configured to connect the established the skeleton joints of the human body to form the skeleton model of the human body which tracks, when the human body makes a series of movements, corresponding movements of the human body, and to display tracking of the movements by the skeleton model.

* * * * *